(12) United States Patent
Chao

(10) Patent No.: US 6,425,913 B1
(45) Date of Patent: Jul. 30, 2002

(54) ELECTRICAL HEATING CORRECTING WAIST PAD

(76) Inventor: Richard C. C. Chao, No. 35-3, Lane 165, Sec. 1, Hsin-Sheng S. Rd., Taipei (TW)

(*) Notice: Subject to any disclaimer, the term of this patent is extended or adjusted under 35 U.S.C. 154(b) by 87 days.

(21) Appl. No.: 09/584,530

(22) Filed: Jun. 1, 2000

(51) Int. Cl.[7] .................................................. A61F 7/00
(52) U.S. Cl. ........................ 607/108; 607/96; 607/112
(58) Field of Search ........................... 607/108, 114, 607/112, 111, 110, 109, 99, 98, 96, 43; 602/61, 19, 14, 13, 6, 5, 12; 128/112.1, 106.1, 101.1, 100.1, 99.1, 869, 870, 871, 873, 874; 606/240

(56) References Cited

U.S. PATENT DOCUMENTS

| | | | | |
|---|---|---|---|---|
| 3,420,230 A | * | 1/1969 | Ballard ............................ 602/36 |
| 4,099,524 A | * | 7/1978 | Cueman et al. ................. 602/19 |
| 4,589,407 A | * | 5/1986 | Koledin et al. ............... 128/869 |
| 4,682,588 A | * | 7/1987 | Curlee ........................... 602/13 |
| 4,972,832 A | * | 11/1990 | Trapini et al. ................ 607/108 |
| 5,179,942 A | * | 1/1993 | Drulias et al. ............. 128/101.1 |
| 5,571,039 A | * | 11/1996 | Ford ............................. 450/155 |
| 5,634,891 A | * | 6/1997 | Beczak, Sr. et al. ........... 602/19 |
| 5,718,722 A | * | 2/1998 | Kiefer ........................... 607/98 |
| 5,797,153 A | * | 8/1998 | Amioka .......................... 5/632 |
| 6,066,108 A | * | 5/2000 | Lundberg ...................... 602/23 |
| 6,206,909 B1 | * | 3/2001 | Hanada et al. ............... 607/108 |

* cited by examiner

Primary Examiner—Linda C. M. Dvorak
Assistant Examiner—Kenneth Schopfer
(74) Attorney, Agent, or Firm—Bacon & Thomas

(57) ABSTRACT

An electrical heating correcting waist pad is adhered to the waist of human body for foment and correction. The electrical heating correcting waist pad comprises a heat retaining pad having a surface adhering to the waist of a user, a heat transfer means arranged in the heat retaining pad; and a backing pad assembled to another surface of the heat retaining pad. A plurality of hard plates is installed in the backing pad. Two adjusting strips extend from two ends of the backing pad, and each of the adjusting strip is detachably attached with a sticky portion. Heat is transferred by the heat transfer means of the heat retaining pad, and heat retaining pad is fixed to a correct position on the waist of the user, and thus, an electrical heating correcting waist pad with foment and correction functions is formed, in which the tightness thereof can be adjusted according to the size of the waist.

9 Claims, 7 Drawing Sheets

ELECTRICAL HEATING CORRECTING WAIST PAD

BACKGROUND OF THE INVENTION

The present invention relates to an electrical heating correcting waist pad, and especially to a waist pad adhering to the waist of the user's body for foment and correction.

The waist ache has become a popular sickness because of sitting for a long time or bad pose. In general, the correction is performed at night as people sleeps on a hard bed plate or ground plate. Furthermore, foment strips or cloths are coated on the ache portion for moderation. However, aforementioned two ways have following defects necessary to be improved, which are:

1. The prior art heat retaining bad is filled with liquid, and then is placed in hot water for boiling to enhance the effect of heat retaining. Then, towel encloses the heat retaining bag for foment. Also, the crystallized heat form a water solution of sodium acetate is used as a heat source and an elastic metal piece is placed in the water solution of sodium acetate. As the user is desired to foment, the metal piece is pressed repeatedly for generating vibration from sound wave so as to induce the crystallized reaction of the sodium acetate, so that the crystallized heat is released continuously, and thus the effect of heat retaining is achieved. However, since the surface of the heat retaining bag transfers heat directly, temperature is difficult to be controlled. Further, heating by hot water induce that the lifetime of the heat retaining bag is reduced greatly and thus it is uneconomical.

2. Although hard bed plates or ground plates have the function of correcting ache in muscle, once the whether become cold or in winter, the cold feeling from the hard bed plates or ground plates can not be endured by anyone. Another, hard bed plates or ground plates can not be acquired anywhere, and they have too large volume to be carried conveniently. Therefore, use of the hard bed plates or ground plates are limited by seasons and locations, and thus are inconvenient.

SUMMARY OF THE INVENTION

Accordingly, the primary object of the present invention is to provide an electrical heating correcting waist pad is adhered to the waist of human body for foment and correction. The electrical heating correcting waist pad comprises a heat retaining pad having a surface adhering to the waist of a user, a heat transfer means being arranged in the heat retaining pad; and a backing pad assembled to another surface of the heat retaining pad. A plurality of hard plates is installed in the backing pad. Two adjusting strips extend from two ends of the backing pad, and each of the adjusting strip is detachably attached with a sticky portion. Heat is transferred by the heat transfer means of the heat retaining pad for fomenting the ache waist to improve the recycling of blood. The heat retaining pad is fixed to a correct position on the waist of the user, thus heat is transferred to the heat retaining pad from the heating pieces. Furthermore, by the two adjusting strips fixing the electrical heating correcting waist pad in position, the muscle, nerves, and joints in the ache portion can be corrected in force. As a result, an electrical heating correcting waist pad can be carried easily and not be confined by whether and positions is formed.

Another object of the present invention is to provide an electrical heating correcting waist pad, wherein foldable grooves are formed between the hard plates of the backing pad for folding the electrical heating correcting waist pad to reduce the volume thereof.

A further object of the present invention is to provide an electrical heating correcting waist pad, wherein the electrical heating correcting waist pad is designed as a lying pad according to the ache portion in human body.

A still object of the present invention is to provide an electrical heating correcting waist pad, wherein two electrical heating correcting waist pads can be combined to be used at the back portion.

The various objects and advantages of the present invention will be more readily understood from the following detailed description when read in conjunction with the appended drawing.

DETAILED DESCRIPTION OF THE PREFERRED EMBODIMENTS

Figure 1:
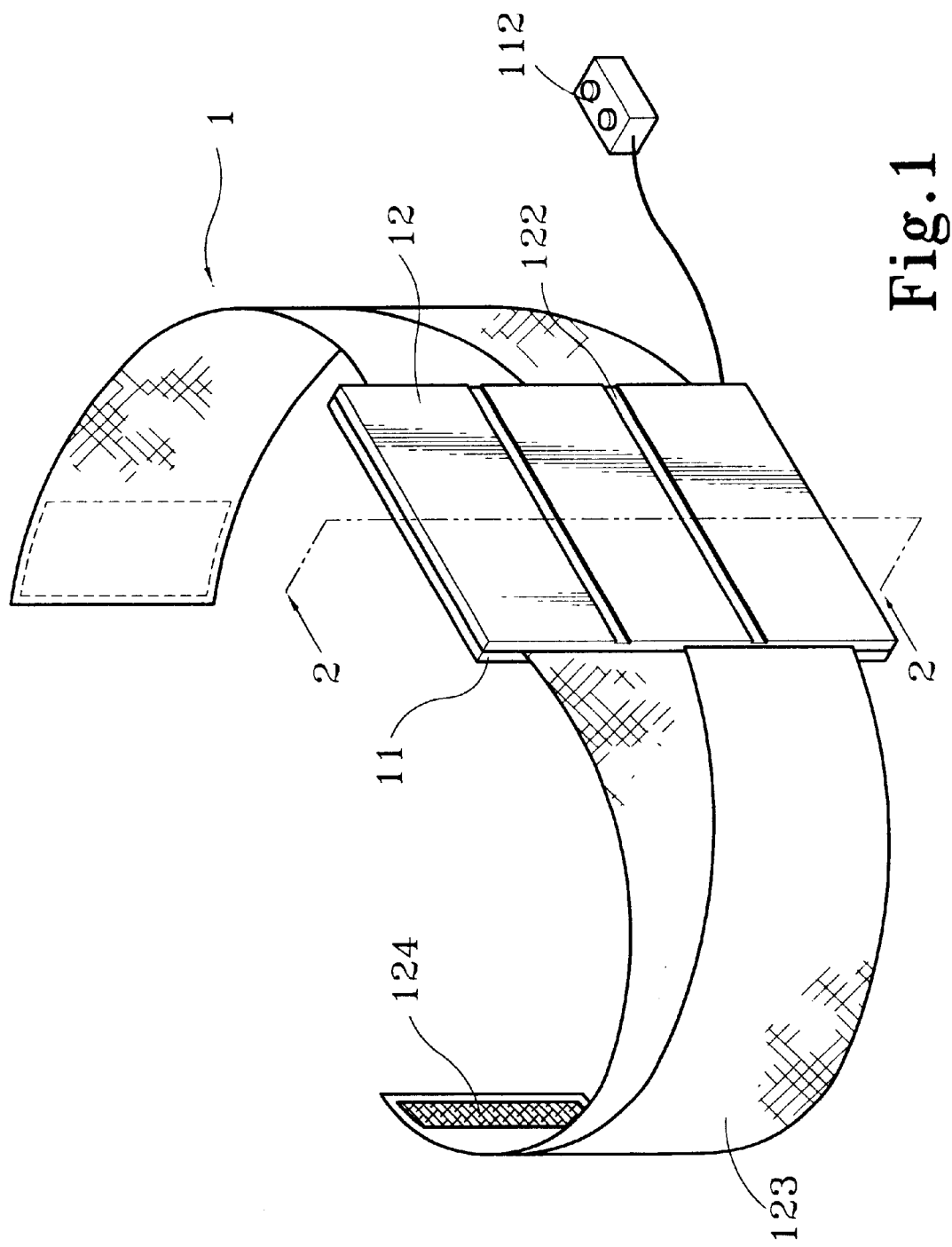
FIG. 1 is a schematic perspective view of the present invention.
Figure 2:
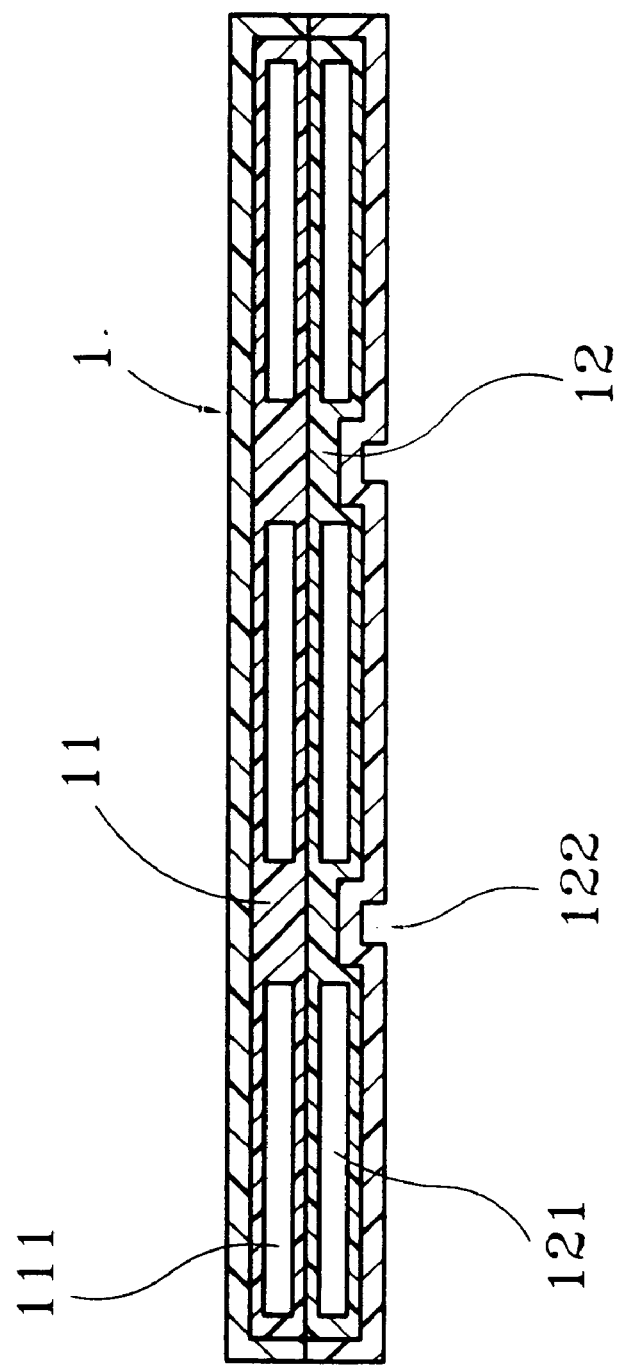
FIG. 2 is a schematic cross sectional view along the line 2—2 of FIG. 1 in the present invention.

With reference to FIGS. 1 and 2, the perspective view and schematic cross sectional view of the present invention are illustrated. As shown in the figures, the electrical heating correcting waist pad 1 of the present invention includes a heat retaining pad 11 adhered to the waist of human body and a set of backing pad 12 at another surface of the heat retaining pad.

The heat retaining pad 11 is made of flexible conductive material and a heat transfer means is installed within the heat retaining pad 11. This heat transfer means includes one heating piece or a plurality of heating pieces 111 which are spaced with an equal distance and are embedded in the heat retaining pad 11, and a controller 112 for controlling the temperature of the heating piece 111. A plurality of hard plates 121 are installed in the backing pad 12, which may be wood plates, aluminum plates or other materials. A foldable groove is formed between the hard plate 121. Two adjusting strips 123 extend from the two ends of the backing pad 12. Each adjusting strip 123 is an elastic band made of elastic material and each of the adjusting strip 123 is detachably attached with a sticky strip 124.

By the heat transfer means of the heat retaining pad 11 to transfer heat and by fixing the backing pad 12 to a correcting position of a human waist, an electrical heating correcting waist pad 1 having function of foment and correction is formed.

Figure 3:
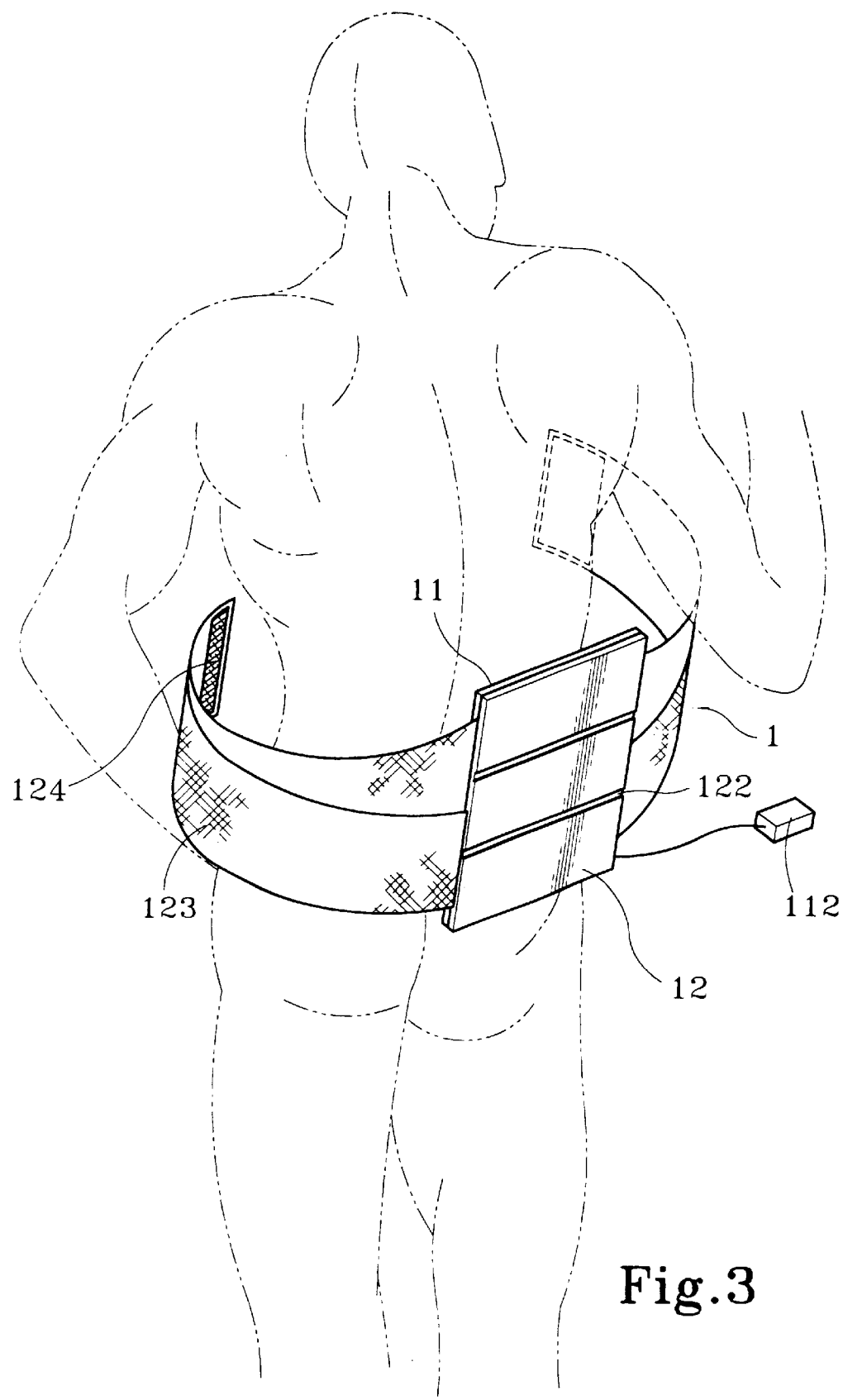
FIG. 3 shows an assembled schematic view of the present invention.

Referring to FIG. 3, an assembled schematic view of the present invention is illustrated. When an ache feeling generates in the waist of the user, the heat retaining pad 11 is adhered to the ache portion at one surface thereof. Then, by the elasticity of the adjusting strip 123 to match the size of the waist, the size is adjusted. Then, the sticky portions 124 at two distal ends of the two adjusting strips 123 are combined and the electrical heating correcting waist pad 11 is fixed on the human waist. Now, by the hard plates 121 in the backing pad 12 to support and fix the pose of human body, and by the two adjusting strips 121 fixing the electrical heating correcting waist pad 1 in position, the muscle, nerves, and joints in the ache portion can be corrected in force. Then, the user can cause the heating pieces 111 to conduct and heat by the controller 112 of the heat transfer means (using a controller 112 to control the heating pieces 111 is well known in the prior art, and thus the details will not further described herein) so as to control the heating temperature and time, and thus heat is transferred to the heat retaining pad 11 from the heating pieces 111 for fomenting the ache waist to improve the recycling of blood. If the user stops to use the electrical heating correcting waist pad, in storage and carrying, since the aforesaid heat retaining pad 11 is made of flexible conductive material, the foldable grooves between the hard plates 121 are used to fold the structure so as to reduce the volume of the electrical heating correcting waist pad 1 for being stored or carried easily.

Figure 4:
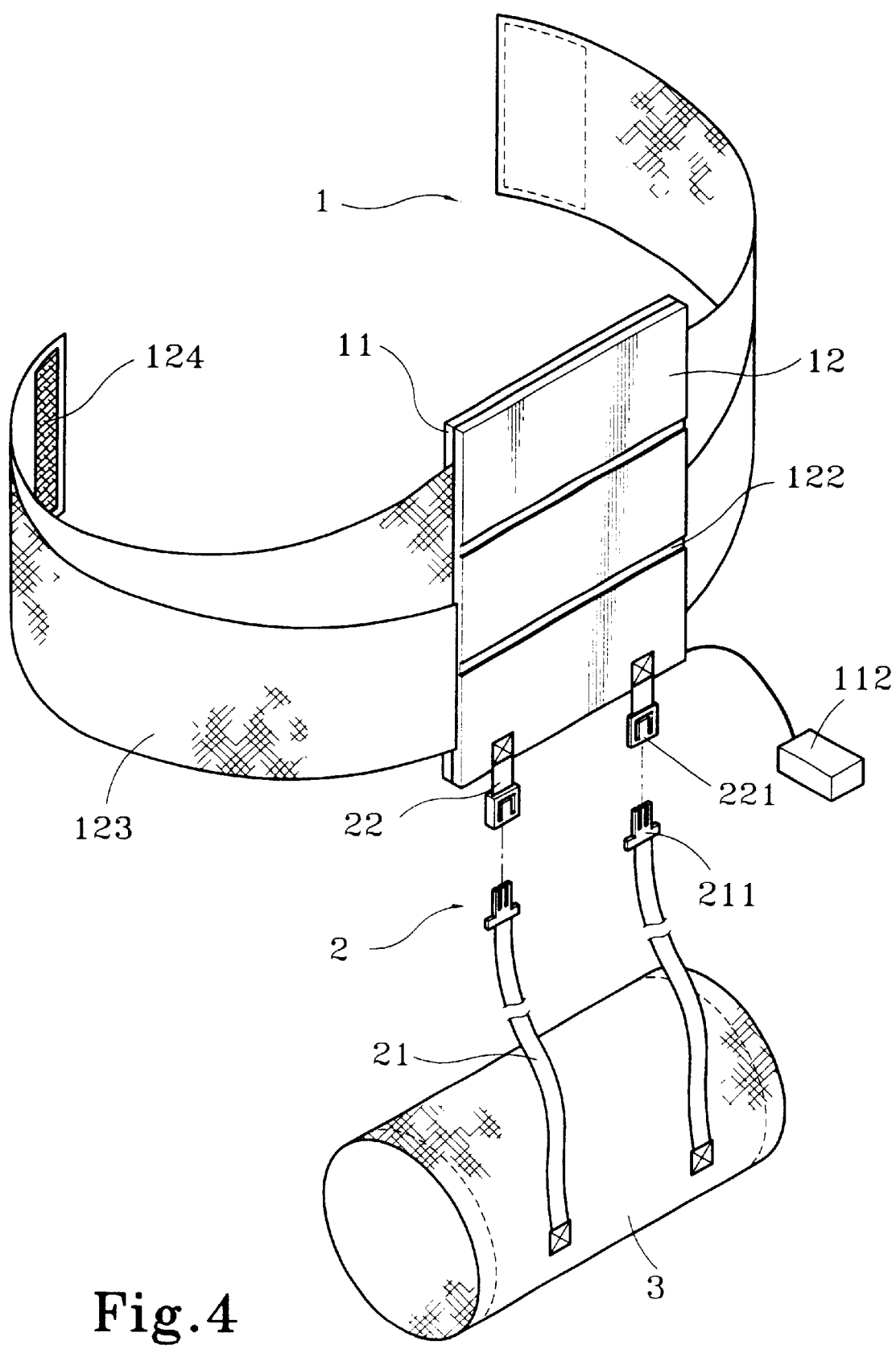
FIG. 4 is a schematic view showing the pillow pad of the present invention.
Figure 5:
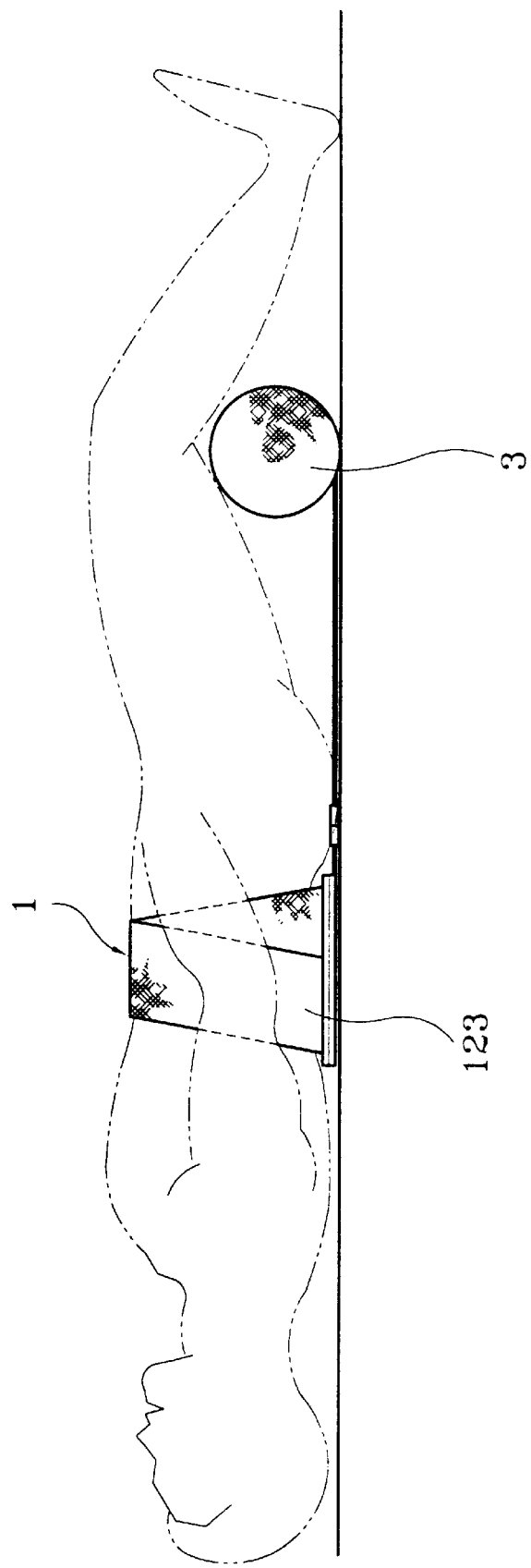
FIG. 5 is a schematic view showing an embodiment of the present invention.

Referring to FIGS. 4 and 5, the schematic views about the embodiment of the present invention is illustrated. As shown in the figures, the electrical heating correcting waist pad 1 can be formed as a waist pad or a lying pad according to the ache portion of human body. One end of the electrical heating correcting waist pad 1 can be connected with a pillow pad 3 through a buckling set 2. The buckling set 2 includes two connecting strips 21 and 22 being connected to the electrical heating correcting waist pad 1 and the pillow pad 3, respectively. The end portions of the two connecting strips 21 and 22 are installed with buckle 211 and buckling seat 221 which may be buckled with one another. By the buckling set 2 to combine with the electrical heating correcting waist pad 1 and pillow pad 3. As the user sits on electrical heating correcting waist pad with the waist pad 1 or lies on the electrical heating correcting waist pad with the lying pad 1, for foment, the knees of the user resists against the pillow pad 3 so as to be in a comfort pose.

Figure 6:
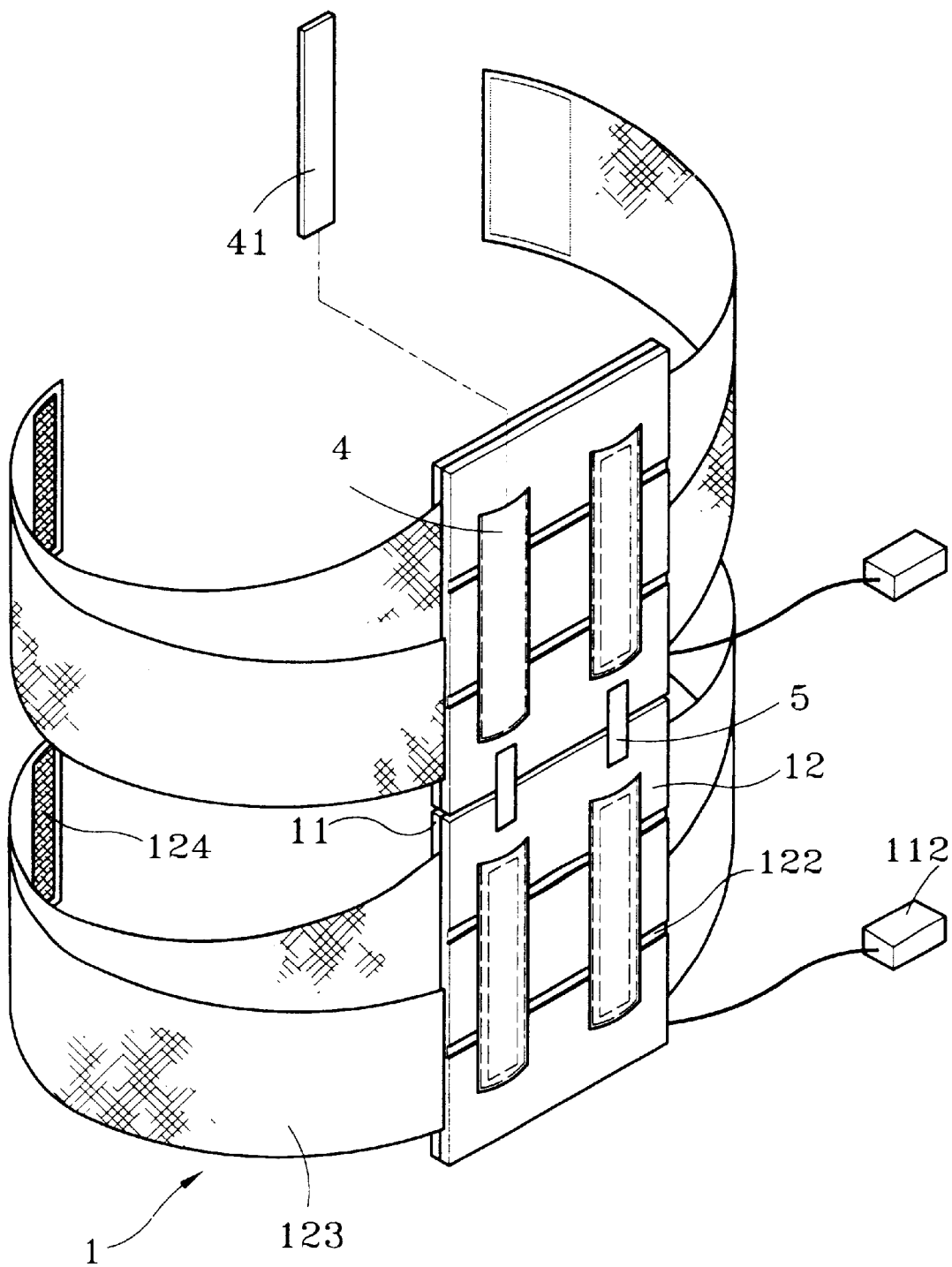
FIG. 6 is another schematic view of an application in the present invention.
Figure 7:
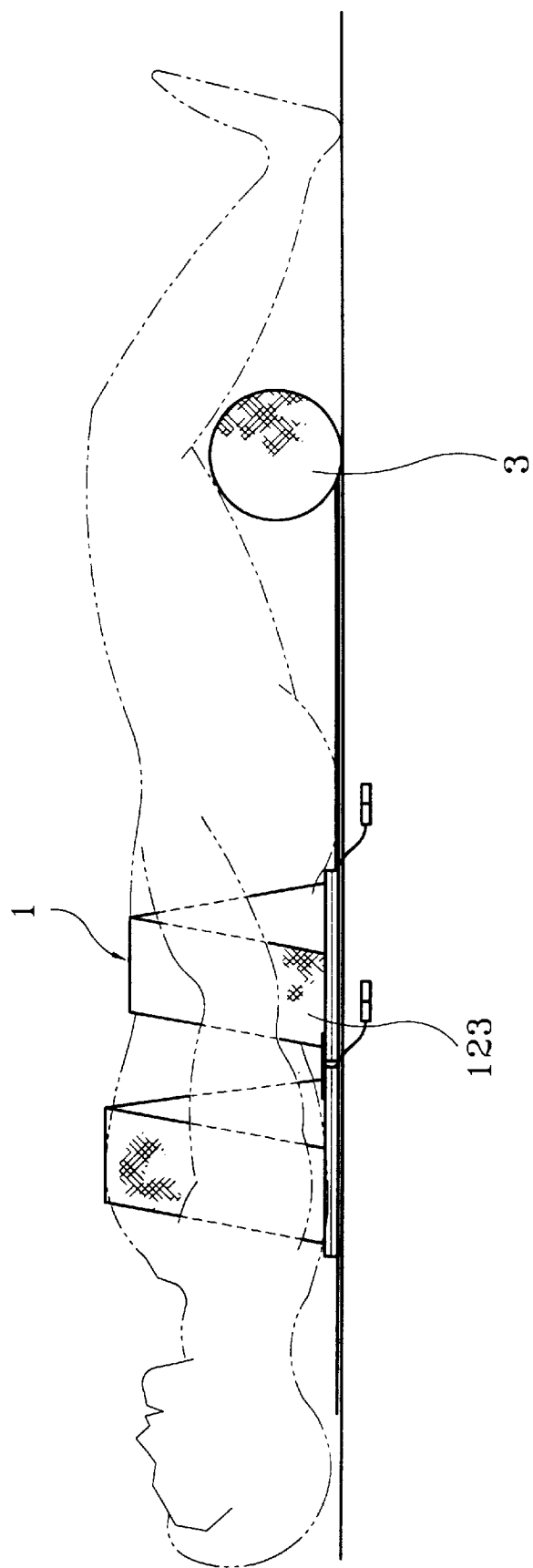
FIG. 7 is a schematic view of another embodiment in embodiment.

Referring to FIGS. 6 and 7, an application and a schematic view of the embodiment of the present invention are illustrated. As shown in the figures, other than to be used singly, the electrical heating correcting waist pad 1 may be installed with a receiving portion 4 symmetric in left and right sides at a proper position, and a hard plate 41 is installed in the receiving portion 4 for firmly supporting the electrical heating correcting waist pad 1 without being bent. A jointing portion 5 is installed at a proper position at one end of the electrical heating correcting waist pad 1. The jointing portion 5 has a pad capable of sticky repeatedly for combining two electrical heating correcting waist pads 1 so that the electrical heating correcting waist pads 1 extends to the waist and back of human body. Further, since the receiving portion is made of soft material, if it is not used, it is only necessary to draw out the hard plate 4 from the receiving portion 4 and then expand the jointing portion 5 for storing the electrical heating correcting waist pad 1.

Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A heating correcting waist pad comprising:
    a heat retaining pad having a first surface arranged to adhere to a waist of a user, and a heat transfer means arranged in the heat retaining pad for transferring heat to the waist of the user through the heat retaining pad; and
    a backing pad assembled to a second surface of the heat retaining pad, a plurality of hard plates being installed in the backing pad; and two adjusting straps extending from two ends of the backing pad, respective ends of each of the adjusting straps being detachably attached to each other by means of a sticky portion on said respective ends;
    wherein said heat retaining pad is fixed to a correct position on the waist of the user, and
    wherein said hard plates are oriented horizontally and separated by grooves arranged to permit folding of the backing pad when the waist pad is not in use, and further comprising at least one rigid stay and at least one vertically oriented receiving portion extending across a plurality of said hard plates for removably receiving said stay in order to prevent said backing pad from being folded when the waist pad is in use.

2. The heating correcting waist pad as claimed in claim 1, wherein the heat transfer means includes one or more heating elements and a controller for controlling the heating elements.

3. The heating correcting waist pad as claimed in claim 1, wherein the adjusting straps are elastic bands made of an elastic material.

4. The heating correcting waist pad as claimed in claim 1, wherein the hard plates are wood plates or aluminum plates.

5. The heating correcting waist pad as claimed in claim 1, wherein the heating correcting waist pad is arranged to be used as a lying pad according to an ache portion in the user.

6. The heating correcting waist pad as claimed in claim 1, wherein one end of the heating correcting waist pad is connected to a pillow pad through a buckling ring, said pillow pad being arranged to position knees of the user.

7. A heating correcting waist pad comprising:
    a heat retaining pad having a first surface arranged to adhere to a waist of a user, and a heat transfer means arranged in the heat retaining pad for transferring heat to the waist of the user through the heat retaining pad; and
    a backing pad assembled to a second surface of the heat retaining pad, a plurality of hard plates being installed in the backing pad; and two adjusting straps extending from two ends of the backing pad, respective ends of each of the adjusting straps being detachably attached to each other by means of a sticky portion on said respective ends, and a joining portion being installed at one end of said backing pad, said joining portion being arranged to enable said backing pad to be joined to the backing pad of a second said heating correcting waist pad to transfer heat to a back of the user as well as to the user's waist;
    wherein said hard plates are oriented horizontally and separated by grooves arranged to permit folding of the backing pad when the waist pad is not in use, and further comprising at least one rigid stay and at least one vertically oriented receiving portion extending across a plurality of said hard plates for removably receiving said stay in order to prevent said backing pad from being folded when the waist pad is in use.

8. The heating correcting waist pad as claimed in claim 1, wherein the receiving portion is made of soft material.

9. The heating correcting waist pad as claimed in claim 7, wherein the joining portion is a pad capable of being stuck repeatedly.

* * * * *